United States Patent
Li et al.

(10) Patent No.: US 10,392,640 B2
(45) Date of Patent: Aug. 27, 2019

(54) METHOD FOR MODIFYING STARCH TO SLOW DOWN THE DIGESTION RATE

(71) Applicants: Zhaofeng Li, Wuxi (CN); Zhengbiao Gu, Wuxi (CN); Junyan Ren, Wuxi (CN); Caiming Li, Wuxi (CN); Li Cheng, Wuxi (CN); Yan Hong, Wuxi (CN)

(72) Inventors: Zhaofeng Li, Wuxi (CN); Zhengbiao Gu, Wuxi (CN); Junyan Ren, Wuxi (CN); Caiming Li, Wuxi (CN); Li Cheng, Wuxi (CN); Yan Hong, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 16/033,214

(22) Filed: Jul. 12, 2018

(65) Prior Publication Data
US 2019/0177758 A1    Jun. 13, 2019

Related U.S. Application Data

(63) Continuation of application No. PCT/CN2017/117786, filed on Dec. 21, 2017.

(30) Foreign Application Priority Data

Dec. 11, 2017 (CN) .......................... 2017 1 1304745

(51) Int. Cl.
| | |
|---|---|
| *C12P 19/18* | (2006.01) |
| *C12N 9/10* | (2006.01) |
| *A23L 33/21* | (2016.01) |
| *A23L 29/212* | (2016.01) |

(52) U.S. Cl.
CPC .............. *C12P 19/18* (2013.01); *A23L 29/212* (2016.08); *A23L 33/21* (2016.08); *C12N 9/107* (2013.01); *A23V 2002/00* (2013.01)

(58) Field of Classification Search
None
See application file for complete search history.

(56) References Cited

PUBLICATIONS

Li. Relationship between structure and retrogradation properties of corn starch treated with 1,4-a-glucan branching enzyme. Food Hydrocolloids 52 (2016) 868-875.*

* cited by examiner

*Primary Examiner* — Yong D Pak
(74) *Attorney, Agent, or Firm* — Lili Chen

(57) ABSTRACT

Disclosed is a method for modifying starch to slow down the digestion rate of modified starch. The present invention utilizes two-stage GBE treatment to convert the long straight-chain starch molecules into highly branched molecules with compact structures so as to decrease the digestion rate of the starch. During the two-stage treatment, granular starch was first treated with GBE, the treated starch was gelatinized in boiling water, and the gelatinized starch was treated with GBE for a second time, leading to an enhanced effect of GBE modification. Compared with the one-staged GBE modification, the two-stage GBE modification can further increase the content of slowly digestible starch in the modified starch and thus decrease the digestion rate of starch.

7 Claims, No Drawings
Specification includes a Sequence Listing.

METHOD FOR MODIFYING STARCH TO SLOW DOWN THE DIGESTION RATE

CROSS-REFERENCES AND RELATED APPLICATIONS

This application claims priority to, and is a continuation of international application No. PCT/CN2017/117786, entitled "A Method for Modifying Starch to Slow Down the Digestion Rate", filed Dec. 21, 2017, and claims priority to Chinese application No. 201711304745.7, filed Dec. 11, 2017, the content of both applications are herein incorporated by reference in their entirety.

BACKGROUND OF THE INVENTION

Field of the Invention

The present invention relates to a method for modifying starch to slow down the digestion rate, which belongs to the field of modified starch.

Description of the Art

Starch, as a main source of energy for humans and most animals, is commonly used in food, medicine, textile and other industrial fields. In today's society, consumers are increasingly pursuing higher quality nutrition. Foods, which can maintain satiety and provide energy continuously and slowly after intake, satisfy the needs of consumers. The slowly digestible starch, which is slowly absorbed after being ingested by the human body, provides sustained release of energy to avoid the severe fluctuation of the blood sugar. Conforming to the trend of food development, it has great market potential as a raw material for food.

However, in the process of food processing, such as heating, irradiation, and decoction, the structure of starch granules is destroyed and the slow digestibility of the processed starch is drastically reduced, making it difficult to meet the requirements of modern consumers. The modification of starch by physical, chemical or biological methods can change the molecular structure of starch, thereby improving the digestibility of starch and meeting the needs of a healthy diet. Biological methods, which have the advantage of substrate specificity, are most widely used.

Starch branching enzyme (BE; EC 2.4.1.18) is a glycosyltransferase belonging to glycoside hydrolase 13. It firstly hydrolyzes $\alpha$-1,4 glycosidic bonds on the substrate molecule and cleaves straight-chain dextran. It, in turn, transfers the sugar chain fragments to the remaining substrate molecules by transglycosylation, forming $\alpha$-1,6 glycosidic bonds.

In the previous report, the method of starch modification using the starch branching enzyme are relatively simple, and still has room for improvement. The invention improves the slow digestibility of the modified starch by optimizing the enzymatic modification process.

SUMMARY OF THE INVENTION

In order to increase the percentage of slow-digested starch, the present invention provides a starch modification method for reducing the starch digestion rate. The starch molecular structure is changed by the starch branching enzyme (GBE) to generate starch molecules with shorter and more branches so as to slow down the digestion rate of the starch. More importantly, the invention provides a two-stage modification strategy. The first step is to use granular starch as a substrate for modification, followed by gelatinization of the product. Secondly, the gelatinized starch is used as a substrate for two-stage modification to obtain starch with improved property. The two-stage GBE modification strategy can further increase the content of slow-digested starch in the modified starch, and reduce the starch digestion rate.

In one embodiment, the present invention provides a enzymatic modification method for increasing the content of slowly digestible starch in the modified starch, comprising the steps as follows. After being preheated under 50° C. to 60° C. for 10 to 15 minutes, 20 U/g to 50 U/g GBE is added to a starch slurry sample, and the sample is treated under 50° C. to 60° C. for 4 to 20 hours. After heated in boiling water bath for 30 minutes, the starch sample is heated under 50° C. to 60° C. for 10 to 15 minutes before adding 20 U/g to 50 U/g GBE. The starch sample is then treated under 50° C. to 60° C. for 4 to 20 hours, and heated in a boiling water bath for 30 minutes. The reaction is terminated, and the final modified starch is obtained after being dried.

In one embodiment of the present invention, after being preheated under 50° C. to 60° C. for 10 minutes, 20 U/g to 50 U/g GBE is added to a starch slurry sample, and the sample is treated under 50° C. to 60° C. for 4 to 20 hours. After heated in boiling water bath for 30 minutes, the starch sample is heated under 50° C. to 60° C. for 10 minutes before adding 20 U/g to 50 U/g GBE. The starch sample is then treated under 50° C. to 60° C. for 4 to 20 hours, and heated in a boiling water bath for 30 minutes. The reaction is terminated, and the final modified starch is obtained after being dried.

In one embodiment of the present invention, the starch is ordinary corn starch.

In one embodiment of the present invention, the mass concentration of the starch slurry is 5%.

In one embodiment of the present invention, the pH of the starch milk is regulated to 7.0 to 8.0.

In one embodiment of the present invention, the amount of the added GBE is 20-50 U/g of starch on a dry basis.

In one embodiment of the present invention, the sample added with GBE is treated under a constant temperature between 50° C. to 60° C.

In one embodiment of the present invention, GBE is derived from *Geobacillus thermoglucosidans* STB02, wherein the GBE is the starch branching enzyme disclosed in Chinese patent application No. 201610345583, encoded by a GBE gene having the DNA sequence of SEQ ID NO:1.

Advantages of the present invention are as follows. The present invention utilizes starch branching enzymes to convert long starch molecules into compact branched ones, thereby slowing down the rate of starch digestion. By controlling the modification substrate, the granular starch was first used as a substrate for enzymatic modification, and the product was then gelatinized. The gelatinized starch was used as a substrate for modification in the second stage to further increase the structral change of the modified starch. The two-stage modification method can reduce the rate of starch digestion, providing new strategies for preparing slowly digestible starch by biological modification.

DETAILED DESCRIPTION

Determination Method of Starch Digestibility

Weigh 0.6 g of starch and 50 mg of guar gum in a centrifuge tube, add 10 mL of pepsin (5 mg/mL enzyme solution in 0.05 M HCl), and shake at 160 r/min in a 37° C. water bath. After 30 min, add 10.0 ml of 0.25M sodium acetate buffer and 30 glass beads (d=5 mm), and then mix 5 mL of enzyme solution (amylem amylase $6.45 \times 10^4$ Ceralpha Units/g starch, saccharification enzyme 167 U/g starch), and react in a 37° C. water bath.

After 20 minutes and 120 minutes of reaction respectively, 250 μL of reaction mixture was mixed with 10 mL of 66.6% ethanol. The mixture was centrifuged at 3500 rpm for 5 min, and 100 μL of supernatant was assayed for glucose content (Glucose oxidase GOPOD method). In addition, after 120 min of reaction, the sample was mixed and placed in a boiling water bath for 30 min. After cooling, 10.0 ml of 7M KOH was added and the mixture was placed in 4° C. for 30 min.

Take 0.5 ml of the above mixture in 5.0 mL of 0.5 M acetic acid and add 84 μL of amyloglucosidase for 30 min at 70° C. and boil for 10 min. Dilute with 20 mL of water and centrifuge at 1500 rpm for 5 min. Take 0.1 mL of supernatant for glucose determination. The specific formula is as follows:

$$RDS = G_{20} \times 0.9$$

$$SDS = (G_{120} - G_{20}) \times 0.9$$

$$RS = (TG - G_{120}) \times 0.9$$

In the Formulas:
RDS—Rapidly digestible starch content;
SDS—Slowly digestible starch content;
RS—Resistant starch content;
$G_{20}$—Glucose content produced after 20 minutes of amylorrhexis;
$G_{120}$—Glucose content produced after 120 minutes of amylorrhexis;
TG—Total glucose content in starch after enzyme hydrolysis

COMPARATIVE EXAMPLE 1

Effect of GBE Modification on Slowly Digestible Starch Content in Starch Slurry

Corn starch was dissolved in water to prepare a 5% of starch slurry. After being preheated under 50° C. for 10 minutes, 30U/g GBE, which is the starch branching enzyme disclosed in Chinese patent application No. 201610345583, encoded by a GBE gene having the DNA sequence of SEQ ID NO:1, was added, and the mixture was treated under 50° C. for 10 hours. The reaction was terminated after heating the mixture in boiling water for 30 minutes. The modified starch was obtained after freeze-drying. The digestion property of modified starch was shown in Table 1.

The result shows that GBE modification can improve the digestion property of the corn starch. After a 10 hr GBE treatment, the RDS content of modified starch is significantly decreased, while the SDS content and RS content are significantly increased. After GBE modification, the RDS content of starch is 8.4% lower than that of control (without GBE treatment), the SDS content and the RS content of starch are 29.5% and 17.5% higher than that of control, respectively. It indicated that GBE modification can improve the slow digestion property of the product. The highly branched structure and the shorter chains generated during modification increases the steric hindrance of the starch, slowing down the digestive hydrolysis of enzyme. However, the SDS content of modified starch is not high enough to meet the requirements of customers. So there is still room for further improvement.

COMPARATIVE EXAMPLE 2

Effect of GBE Modification on Slowly Digestible Starch Content in Gelatinized Starch Corn starch was dissolved in water to prepare a 5% of starch slurry. After 30 minutes of gelatinization in boiling water, the starch slurry was incubated under 50° C. for 10 minutes. 30 U/g GBE was added and the mixture was treated under 50° C. for 10 hours. The starch sample was boiled for 30 minutes to terminate the reaction. The modified starch is obtained after freeze drying. The digestion property of the modified starch is shown in Table 1.

The result in Table 1 shows that after a 10 hr GBE treatment of gelatinized corn starch, the SDS content of modified starch reaches 24.6%, and is 77.0% higher than that of control and 36.7% higher than that of the comparative Example 1 (using the corn starch granules as the substrate). The RDS content of modified starch is 20.4% lower than that of control and 13.1% lower than that of the comparative Example 1.

COMPARATIVE EXAMPLE 3

Effect of GBE Modification on Slowly Digestible Starch Content in Gelatinized Starch Corn starch was dissolved in water to make a 5% of starch slurry. After being gelatinizing in boiling water for 30 min and being incubating 50° C. for 20 min, 30 U/g GBE was added. The starch sample was treated under 50° C. for 20 hours, and the reaction was terminated by placing in a boiling water bath for 30 minutes. The final modified starch was obtained after freeze drying. The digestion property of the modified starch is shown in Table 1.

The result shows that after a 20 hr GBE treatment of gelatinized corn starch, the SDS content of modified starch reaches 25.4%, and is 82.7% higher than that of untreated control and 15.0% higher than that of the comparative Example 1 (using corn starch granules as the substrate). It shows that in comparison with the method using granular starch as the substrate, the GBE modification method using gelatinized starch as the substrate gives better results. The destruction of starch granules by gelatinization facilitates the branching reaction of GBE and starch, and significantly improves the slow digestibility of the final product of the modified starch.

EXAMPLE 1

Effect of Two-Stage Modification on Slowly Digestible Starch Content in Starch

Corn starch was dissolved in water to prepare a 5% of starch slurry. After being preheated under 50° C. for 10 minutes, 30 U/g GBE is added, and then the sample was treated under 50° C. for 10 hours. After being heated in boiling water bath for 30 minutes, the sample is preheated under 50° C. for 10 minutes, and then 30 U/g GBE is added. After 6 hours of treatment under 50° C., the enzymatic reaction was terminated by a boiling water bath. The modified starch was obtained after freeze-drying. The digestion property of modified starch is shown in table 1.

The result shows that after the two-stage modification, the SDS content of modified starch reaches 26.0%, which is 87.0% higher than that of untreated control and 2.4% higher than that of the comparative Example 3 (using gelatinized corn starch as the substrate); and the RDS content of modified starch is 23.9% lower than that of control and 2.3% lower than that of the comparative Example 3.

EXAMPLE 2

Effect of Two-stage Modification on Slowly Digestible Starch Content in Starch

Corn starch is dissolved in water to prepare a 5% of starch slurry. After being preheated under 50° C. for 10 minutes, 30 U/g GBE was added, and then the sample was treated under 50° C. for 10 hours. The sample was heated in boiling water bath for 30 minutes and incubated under 50° C. for 10 minutes, and 30 U/g GBE was then added. After 8 hours of treatment under 50° C., the enzymatic reaction was terminated by incubation in a boiling water bath. The modified starch was obtained after freeze-drying. The digestion property of modified starch is shown in Table 1.

The result shows that after the two-stage modification, the RDS content of modified starch reaches 54.8%, which is 5.0% lower than that of the comparative Example 3 (using gelatinized corn starch as the substrate); the SDS content of modified starch reaches 26.3%, which is 3.5% higher than that of the comparative Example. The RS content of modified starch is 11.8% higher than that of the comparative Example 3.

EXAMPLE 3

Effect of Two-stage Modification on Slowly Digestible Starch Content in Starch

Corn starch was dissolved in water to prepare a 5% of starch slurry. After being preheated under 50° C. for 10 minutes, 30 U/g GBE was added and the sample was treated under 50° C. for 10 hours. After the sample was heated in a boiling water bath for 30 minutes and incubated under 50° C. for 10 minutes, 30 U/g GBE was added to the sample and treated at 50° C. for 10 hours. The enzymatic reaction was terminated by incubation in a boiling water bath. The modified starch was obtained after freeze-drying. The digestion property of modified starch is shown in Table 1.

The result shows that after the two-stage modification, the RDS content of modified starch reaches 53.8%, which is 6.8% lower than that of the comparative Example 3 (using gelatinized corn starch as the substrate). The SDS content of modified starch reaches 26.5%, which is 4.3% higher than that of the comparative Example 3. The RS content of modified starch is 16.6% higher than that of the comparative Example 3. The result shows that the two-stage modification process can further decrease the digestion rate of the product, and the slow digestibility of the product will be improved with the increase of gelatinization time.

TABLE 1

| | Digestion property of Modified Samples | | |
| --- | --- | --- | --- |
| | Rapidly Digestible Starch Content (%) | Slowly Digestible Starch Content (%) | Resistant starch content (%) |
| Comparative Example 1 | 67.9 ± 0.3 | 18.0 ± 0.7 | 14.1 ± 0.6 |
| Comparative Example 2 | 59.0 ± 0.7 | 24.6 ± 0.9 | 16.4 ± 0.7 |
| Comparative Example 3 | 57.7 ± 0.6 | 25.4 ± 0.7 | 16.9 ± 0.9 |
| Example 1 | 56.4 ± 0.7 | 26.0 ± 0.7 | 17.6 ± 0.5 |
| Example 2 | 54.8 ± 0.2 | 26.3 ± 0.7 | 18.9 ± 0.4 |
| Example 3 | 53.8 ± 0.6 | 26.5 ± 0.3 | 19.7 ± 0.3 |
| Untreated Control | 74.1 ± 0.1 | 13.9 ± 0.8 | 12.0 ± 0.8 |

During the two-staged GBE modification, the granular starch was first treated with GBE, and the sample was then heated in boiling water for 30 minutes, the gelatinized product was treated with GBE for a second time. The result shows that the RDS content of modified starch prepared from the two-stage modification method is 53.8%, which is 27.4% lower than that of control; the SDS content of modified starch reaches 26.5%, which is 90.6% higher than that of control; and the RS content of modified starch is 64.2% higher than that of control. Compared with the modification method directly using gelatinized starch as the substrate, the two-stage modification strategy can further increase the SDS content of modified starch, providing a strategy to effectively increase the SDS content of modified starch products.

The above results show that the use of starch branching enzymes to modify the starch can increase the SDS content of modified starch and improve the digestibility of starch after gelatinization. More importantly, the two-stage modification strategy can effectively improve the modification effect of starch branching enzymes and significantly slow down the digestion rate of starch.

What is claimed is:

1. A method to modify starch to slow down the digestion rate of the starch, comprising the sequential steps of:
   a) heating a starch slurry sample at 50 to 60° C. for 10 to 15 minutes and then adding 20 to 50 U/g starch branching enzyme (GBE) to the starch slurry sample, wherein the GBE is encoded by a GBE gene having the DNA sequence of SEQ ID NO:1;
   b) incubating the starch slurry sample with the GBE at 50 to 60° C. for 4 to 20 hours;
   c) heating the starch slurry sample in boiling water to obtain a gelatinized starch and inactivate the GBE;
   d) incubating the gelatinized starch at 50 to 60° C. for 10 to 15 minutes and then adding 20 to 50 U/g of the GBE to the gelatinized starch;
   e) incubating the gelatinized starch with the GBE at 50 to 60° C. for 4 to 20 hours;
   f) heating the gelatinized starch in boiling water to terminate the enzymatic reaction; and
   g) obtaining final product of modified starch after freeze-drying.

2. The method of claim 1, wherein the starch slurry sample is heated at 50-60° C. for 10 min in step a) and the gelatinized starch is heated at 50 to 60° C. for 10 minutes in step d), and the starch slurry sample is heated in boiling water for 30 min in step c).

3. The method of claim 1, wherein the starch is ordinary corn starch.

4. The method of claim 1, wherein the mass concentration of the starch slurry is 5%.

5. The method of claim 1, wherein the pH of the starch slurry is adjusted to 7.0 to 8.0.

6. The method of claim 1, wherein the starch slurry sample is heated at 50° C. for 10 min in step a) and the gelatinized starch is heated at 50 to 60° C. for 10 minutes in step d), wherein the starch slurry sample with the GBE is incubated at 50° C. for 6-10 hr in step b) and the gelatinized starch with the GBE is incubated at 50° C. for 6 to 10 hours in step e), and wherein the starch slurry sample is heated in boiling water for 30 min in step c) and the gelatinized starch is heated in boiling water for 30 min in step f).

7. The method of claim 6, wherein 30 U/g of the GBE is added in step a) and d), and wherein the starch slurry sample with the GBE is incubated at 50° C. for 8-10 hr in step b) and the gelatinized starch with the GBE is incubated at 50° C. for 8 to 10 hours in step e).

* * * * *

SEQUENCE LISTING

```
<160> NUMBER OF SEQ ID NOS: 1

<210> SEQ ID NO 1
<211> LENGTH: 1938
<212> TYPE: DNA
<213> ORGANISM: Geobacillus thermoglueosidan STB02

<400> SEQUENCE: 1
catatgagcg ttgtccctcc gaccgatctg gaaatttatt tatttcacga aggcagctta      60
tataaaagtt atgaattgtt tggcgcgcat gtgataaaac aaaacgacgt tgtcggaacc     120
cggttttgcg tatgggctcc gcatgcgcgg caagtgcggt tagtcggcag tttttaatgac    180
```

```
tggaacggaa ctaattttaa tcttgtaaaa gtaagtaatc aaggtgtatg gacgatttt    240 attccgaaa  acttggaagg gcatttatat aaatacgaaa ttaccactag cgatggaaat   300
gtcgtgttaa aagcagatcc atacgcgttt cactccgaat tgcgccccg  tactgcctcc   360 atcgtctacg acataaaagg ttatcaatgg aatgaccaaa catggcgacg gaagaaacag   420
cgaaagcgaa tatatgacca gcctttgttc atttatgagc ttcacttcgg ttcgtggaaa   480
aagaaagaaa acggcaattt ttatacatat cgggagatgg cagatgagtt acttccatac   540
gtgatggaac atggttttac ccacattgaa ttgcttccgc tcgttgaaca tccgcttgac   600
cgctcctggg gatatcaagg aacaggttat tattcagcaa caagccgcta cgggacgccg   660
catgatttga tgcattttat tgatcgcttc catcaagcgg gcattggcgt cattttcgat   720
tgggttcccg gccacttttg caaagatgaa catggattat acatgtttga tggagcaccg   780
acatacgaat atgacaacat acaagatcgg gaaaatggcg aatggggcac ggcgaatttt   840
gatcttggca agccggaagt ccgcagcttt ttgatttcca atgcgttgtt ttggatggaa   900
tatttccacg tcgacggatt tcgggtggat gcggtggcca atatgctgta ttggccaaat   960
agagaggcag cacagcaaaa cccgcatgct gttcagtttt tgcaaaaatt aaatgagacc  1020
gtatttgcgc atgacccggg catattgatg attgccgaag attcgacgga atggccgctc  1080
gtcactgctc caacgtatgc cggagggctg gggtttaact ataaatggaa catggggtgg  1140
atgaacgata ttttaacata tatggaaacg gcgccggaga agcgaaaaca tgtgcacaat  1200
aaagtaacct tttcccttt  gtacgcgtat tcggaaaatt ttattttacc tttttcccac  1260
gatgaggtcg tgcatggaaa aaaatcgctg ctaaataaaa tgccggggac gtatgaggaa  1320
aagtttgcac aattaaggct gctgtatggg tatttgctaa cacatcccgg caagaaacta  1380
ttgtttatgg gcggcgaatt tgcccagttt gatgagtgga aggatgcaga gcagctggat  1440
tggatgcttt ttgatttcga gatgcaccag aaaatgaata tgtacgtgaa agcattattg  1500
aaatgttata agcgctgcaa atctttgtat gagctagacc attctccaga cgggtttgag  1560
tggattgatg ttcataacgc tgaacaaagt attttctcat ttgtccgcag aggaaaaaaa  1620
gaaaacgatt tgcttgttgt cgtgtgcaat tttaccagta aagtgtatca cgattataaa  1680
gttggcgttc cgctatttgc caaataccgg gaaatcatca gcagcgatgc ggccaaattc  1740 gggggtggg  gcaatgtcaa tgcaaagccg gttgcggcga gcaaagaacc gtttcatgga  1800
aagccgtatc atattcgcat gacggttccg ccgtttggca tttccatttt aagaccagtg  1860 aaaaacggg  gggagagaag cgttgatggc aaagaaaaag tgcatcgcca tgttattggc  1920
gggagggcaa ggctcgag                                                1938
```